United States Patent [19]

Lahr

[11] Patent Number: 5,378,470
[45] Date of Patent: Jan. 3, 1995

[54] RECTALLY ADMINISTERED PHARMACEUTICAL PREPARATION

[75] Inventor: Wolfgang Lahr, Berlin, Germany

[73] Assignee: Henning Berlin GmbH, Berlin, Germany

[21] Appl. No.: 173,697

[22] Filed: Dec. 20, 1993

Related U.S. Application Data

[63] Continuation of Ser. No. 663,833, Mar. 22, 1991, abandoned.

[30] Foreign Application Priority Data

Jul. 25, 1989 [DE] Germany ............... 3924570

[51] Int. Cl.⁶ .................................... A61K 9/02
[52] U.S. Cl. .......................... 424/436; 424/DIG. 15; 514/966
[58] Field of Search ............... 424/436, DIG. 15; 514/966

[56] References Cited

U.S. PATENT DOCUMENTS 4,664,256  5/1987  Halskov ............... 206/213.1
4,678,516  7/1987  Alderman et al. ...... 424/DIG. 15

FOREIGN PATENT DOCUMENTS 0050981  5/1982  European Pat. Off. .
0055313  7/1982  European Pat. Off. .
0062000  10/1982 European Pat. Off. .
8601578  7/1986  European Pat. Off. .
2381520  9/1978  France .
2430227  3/1980  France .
3106619  9/1982  Germany .
3807714  2/1989  Germany .

*Primary Examiner*—Thurman K. Page
*Assistant Examiner*—Carlos Azpuru
*Attorney, Agent, or Firm*—Henry M. Feiereisen

[57] ABSTRACT

Described are dry pharmaceutical preparations or clysters designed for rectal administration, which contain an active ingredient or mixture of active ingredients plus additives, and which are only reconstituted immediately before use by the addition of water, the volume of which can be selected to suit the particular patient. Such preparations are preferably marketed in graduated clyster flasks allowing the contents to be diluted with an amount of water appropriate to a particular patient.

9 Claims, No Drawings

RECTALLY ADMINISTERED PHARMACEUTICAL PREPARATION

This is a continuation of application Ser. No. 07/663,833, filed Mar. 22, 1991, which is now abandoned.

The invention refers to a rectally administered pharmaceutical preparation which is administered in form of an aqueous solution, emulsion or suspension of an active ingredient or mixture of active ingredients, i.e. as enema (clysters). The instant invention thus refers to a new form of medication for therapeutic application in the human field as well as in the veterinary field.

The relevant prior art is characterized by conventional clysters which are prepared as so-called finished clysters, thus representing already the liquid form.

The most striking drawback of finished clysters resides in the fact that they constitute a fixed volume. This volume must be completely administered in order to render the entire dosage of active ingredient effective over a longest possible period. Anatomically and/or pathologically, this causes problems in patients. At reduced resorption ability of the patient, the medication will be rapidly discharged completely or partially.

For pharmacological reasons, finished clysters contain primarily water as liquid phase. However, aqueous systems are prone to microbic attack during production, bottling and storage so that preservatives must be added which in turn have a high allergic capability, are instable in aqueous solutions (e.g. the most frequently used benzoic acid esters are sensitive to hydrolysis) and are absorbed by the plastic material which the clyster bottles are made of (compare Wallhäusser, Praxis der Sterilisation, Thieme-Verlag, 1984, p. 333, 380).

Frequently, finished clysters further contain stabilizers for chemical stabilization of the active ingredients against hydrolysis, oxidation and/or other rearrangement reactions as well as anticaking additives in order to avoid a sedimentation of the active ingredients in suspensions and to ensure a resuspension after sedimentation. In the event that no stabilizers or preservatives are used, particular storage instructions (e.g. "keep refrigerated") and a limited storage stability (expiration date) must be observed for such pharmaceuticals.

Canadian patent 1,230,056 describes clysters of 5-aminosalicylic acid as relevant state of the art which are made as solution or suspension with addition of complexing agents, anti-oxidants and under inert gas.

Mulder et al, Scand. J. of Gastroentero., 1988, 23, p. 1006, describes clysters made of 5-aminosalicylic acid and prednisolone phosphate sodium salt and twice the amount of methylhydroxy benzoate as preservative, based upon the active ingredient prednisolone phosphate, with the stability of such clysters even at 4° C. being guaranteed for only four weeks. Bondesen et al., Scand. J. of Gastroentero., 1984, vol. 19, no. 5, p. 197, describes 5-aminosalicylic acid based clysters in which complexing agents, antioxidants and preservatives are used. Lancet of 3-13-1982, p. 579, teaches finished clysters of beclomethasone dipropionate supplemented with preservatives propylhydroxy benzoate and ethylhydroxy benzoate. All clysters known from this prior art have the drawbacks as set forth above as well as the characteristic economical drawback for finished clysters which is the high weight, relative to the active ingredient, which in turn results in high transport costs.

It is an object of the present invention to provide pharmaceutical preparations for rectal administration in form of an aqueous solution, emulsion or suspension of an active ingredient or mixture of active ingredients so as to allow provision of a volume dosage suited for a particular patient with simultaneous administration of the complete dose of active ingredient and to attain an improved storage stability without employing preservatives and stabilizers.

This object is attained according to the present invention by a rectally administered pharmaceutical preparation which is administered in the form of an aqueous solution, emulsion or suspension of an active substance or mixture of active substances, characterized in that the preparation is solid and contains 0.01 to 95 weight-% of an active substance or a mixture of active substances as well as 99.99 to 5 weight-% adjuvants, respectively based on the overall weight of the solid preparation, of which 2.5–50 weight-% is represented by a hydrophilic gelatinizing agent and/or 0.1–10 weight-% is represented by a waterfree antifoam agent and the preparation has a moisture content of less than 15% respectively calculated on the total weight of the solid preparation.

Advantageous embodiments of such a preparation as well as advantageous applications are referred to in the subclaims.

The present invention is based on the determination to formulate dry clyster preparations which are free of preservatives and are "cold water-soluble" which means within the scope of the invention that they are reconstituted immediately before application by addition of water at room temperature or at body temperature, i.e. they are converted to an applicable formulation in form of a solution, emulsion or suspension. By making and commercializing such solid ("dry") preparations in solid form in clyster flasks with suitable graduations, the storage stability is improved, the transport weight is reduced and dissolving or dispersion of the dry preparation is possible within variable, reproducible volumes to suit the individual therapy requirements.

The preparations according to the invention contain, side-by-side, active ingredients or mixtures of active ingredients and additives which enable a dissolution or dispersion of the active ingredients in added water. In view of the different nature of applicable active ingredients, the active ingredient content may vary in preparations according to the invention within very broad limits, ranging from 0.01 to 95% weight-% which represents the possible range of amounts of active ingredients for practical application. The active ingredient content of a particular dry clyster preparation depends primarily on the type and character of the used active ingredient and the dose typically required therapeutically for such active ingredient. The quantity and quality of the additive composition are generally selected in dependence on the particular active ingredient and constitute in general 99.99 to 5 weight-% of the preparation. It is to be noted, however, that the amount of active ingredient and the amount of additive need not add up to 100 weight-% because solid preparations may also contain e.g. certain amounts of moisture. Concerning the impact of the type of active ingredient, administration of hormones is e.g. in the microgram range, of corticoids in the milligram range and of pharmaceuticals such as mesalazine hormones is in amounts of up to several grams per single dose. For that reason, the broad limits as set forth above are obtained for the content of active ingredient and therefore also for the moiety of active ingredient.

Preferably, reconstitution of dry clysters according to the invention is attained after addition of more than 5 ml of "cold" water by shaking. Usually, this would cause formation of a disturbing foam which in accordance to a preferred embodiment of the present invention is avoided by adding an antifoaming agent as active ingredient to the preparation, preferably in an amount ranging from 0.1 to 10 weight-%. Preferably, waterfree antifoaming agents are used, especially preferred are those of silicon base which cause rapid collapse of the foam.

Further, the preparations of dry clysters preferably contain besides active ingredients gelatinizing agents (thickeners) e.g. gelatinizing agents in form of cellulose derivatives, which form a gel structure in water at room temperature or body temperature, regardless as to whether the reconstituted clyster is a solution or a suspension. The preparations according to the invention may contain such gelatinizing agents in considerably greater amounts than conventional liquid preparations, especially when forming the gel structure preferably at body temperature.

Preferred embodiments of preparations according to the invention may further contain wetting agents in order to ensure a rapid wettability of the constituents after addition of water to the dry preparation and to attain a good spreadability within the intestine.

Depending on the respective circumstances, the dry preparation may contain further additives for making solid solutions or as granulating additives or for other purposes. Preferably, such additives are homopolymers or copolymers of vinyl pyrrolidone, vinyl acetate or vinyl alcohol, polyethylene glycols, especially solid polyethylene glycols of mean molecular weight of up to 35,000 or mixtures thereof, as well as other or further hydrocolloids and wetting agents, flow improving agents such as highly dispersed silicon dioxide, solid water soluble acids, buffers and additives for establishing isotonic and physiologically osmotic conditions, such as common salt, dry thinning agents like starch, modified starch, microcrystalline cellulose, dextrin, lactose, sugar and also emulsifiers. The preparation may also contain as constituents of the solid preparation certain fractions of nonvolatile liquid ingredients such as glycerol, propylene glycol, polyethylene glycols with mean molecular weight of up to 600 and mixtures of such additives.

Preparation of dry clyster preparations in accordance with the invention can be formulated in a variety of methods. These methods should yield products which are preferably waterfree and include in any event, based upon the overall weight of the dry preparation, less than 15 weight-% residual moisture, preferably less than 10 weight-%, especially preferred less than 2 weight-% residual moisture, with chemically bound water (crystal water) remaining unconsidered.

Dry clyster preparations may be made in manners known per se by mixing, granulating, grinding, agglomeration, lyophilization, compacting, pressing, spray drying, spray solidification or combined methods, with the structure of the dry preparation and its composition being formulated in such a manner that the reconstitution is carried out by addition of water in a shortest possible time period, preferably in less than 10 min. Reconstitution of the applicable preparation is attained by adding a desired volume of water to the dry preparation and by repeatedly shaking. The reconstitution can be accelerated when the particles of the preparation according to the invention are of fine constitution, with a preferred size of less than 1 mm, preferably of less than 500 μm.

The clyster preparations according to the invention may be made in principle with all active ingredients which are indicated for rectal application to attain a local or also systemic effect. In particular for treatment of disorders of the larger intestines (rectum and colon), e.g. ulcerative colitis, Crohn's disease, proctitis, haemorrhoidal disorders, but also for intestinal sterilization, application of clyster preparations according to the invention have proven to be successful. Suitable active ingredients include glucocorticoid, e.g. betamethasone, beclomethasone, hydrocortisone, prednisolone, oxipurinol, but also 5-aminosalicylic acid derivatives such as 5-aminosalicylic acid, sulphasalazine. Antirheumatics, analgesics, sulfonamides, antibiotics, calcium antagonists, corticoids, sedatives, muscle relaxants, anticephalalgics, spasmolytics or local anesthetics represent further groups of active ingredients which may be used in preparations according to the invention, whereby the active ingredients may be present in form of their free acids, bases, salts, ester, hydrates and as derivatives thereof. If the therapy dictates, it is certainly possible to use combinations of active ingredients, especially of those set forth above.

It has been shown that the use of preservatives can be omitted in preparations according to the invention. Also, stabilizers as well as anticaking additives can be omitted since the preparations are used shortly after reconstitution. There are no particular storage instructions, and the applicability of the formulated medication corresponds to conventional solid dosage forms and is essentially influenced by the stability of the active ingredient in the dry state. The time for reconstitution usually ranges from less than 1 min to 10 min. Thereafter, the preparations according to the invention are ready for application.

In the following, the invention will be described with reference to advantageous nonlimiting exemplified embodiments.

EXAMPLE 1

0.44 g betamethasone-21-phosphate sodium salt are dissolved in 65.56 g molten polyethylene glycol 6000 at 70° C. until becoming clear 33 g hydroxypropylmethyl cellulose (Methocel ®E5) as well as 1.0 g waterfree silicon-based antifoaming agent is added to the melted mass which is cooled either by pouring in layers of about 1 cm thickness or by spray solidification.

In the first-mentioned case, the solidified melted mass is comminuted to a grain size of less than 350μ. Respective amounts of 1.5 g of solidified melted mass, equivalent to 6.6 mg betamethasone-21-phosphate sodium salt, are bottled in clyster flasks with a gradation of 10 to 100 ml. In an experimental run, graded amounts of 10 ml, 20 ml, 50 ml, 100 ml of lukewarm water are filled. After repeated forceful shaking, a nearly clear, slightly opalescing solution is obtained within 30 to 60 seconds. The foam created through shaking collapsed immediately.

EXAMPLE 2

In analogy to example 1, a dry clyster preparation was made of 6.0 g beclomethasone dipropionate, 1988 g polyethylene glycol 6000, 1000 g hydroxypropylmethyl cellulose and 6.0 g waterfree silicon-based antifoaming agent. Doses of 1.5 g solidified melted mass were reconstituted with 10, 20, 50, 100 ml volume of lukewarm water. The clysters were ready for use after 90 seconds. The reconstituted dry clyster had a pH value within the physiologically acceptable range of 5.5 to 6.5. The solubility of the solidified melted mass was microscopically monitored for recrystallization at 400 times magnification. Through contact with water, the solidified melted mass immediately dissolved without observing crystals during the monitoring period which proves that the active ingredient was in the state of a solid dispersion.

EXAMPLE 3

730 g 5-aminosalicylic acid are comminuted with 10.0 g sodium lauryl sulphate (Texapon ®L 100) and 37.0 g waterfree silicon-based antifoaming agent. 183.0 g hydroxypropylmethyl cellulose (Methocel ® K15M) and 40.0 g highly dispersed silicic acid are homogeneously blended in a mixer. The mixture is finely ground by a pinned disk mill and screened to a grain size of less than 500μ. 5.48 g of the dry clyster preparation, equivalent to 4.0 g 5-aminosalicylic acid, are filled in a graduated clyster flask and supplemented with 50 and 100 ml lukewarm water. The reconstitution is attained through shaking after 2 minutes. The highly viscous suspension is essentially free of foam and allows a good adhesiveness to the intestinal wall through afterswelling of the gelatinizing agent.

EXAMPLE 4

752 g 5-aminosalicylic acid are granulated with a solution of 48 g copolymer of vinyl pyrrolidone/vinyl acetate (Kollidon ® VA64) and 200 g distilled water. The dried granulate is comminuted to less than 2000μ and subsequently sprayed in a fluid bed with a solution or emulsion of 65 g hydroxypropylmethyl cellulose (Emcocel K15M), 0.8 g sodium lauryl sulphate and 10 g antifoaming agent in 5 kg water.

The sprayed granulate has a moisture of 0.5% after drying and is comminuted to a grain size of less than 500μ. The dry clyster preparation is bottled in graduated clyster flasks.

EXAMPLE 5

8.468 g sodium oxipurinol monohydrate is homogeneously mixed with 14.4 g sodium dihydrogenphosphate monohydrate, 7.0 g hydroxypropylmethyl cellulose, 1.1 g waterfree silicon-based antifoaming agent and 0.1 g sodium lauryl sulphate. 5.43 g of dried preparation are proportioned in a clyster flask and supplemented to 100 ml volume with lukewarm water. After brief shaking, the created suspension is reconstituted after 2 minutes. The pH value is 6.5. A visual observation within an observation period of 24 hours does not show any sedimentation.

EXAMPLE 6

In analogy to example 2, a dry clyster preparation of 20 g paracetamol, 170 g polyethylene glycol 10.000, 9.5 g hydroxypropylmethyl cellulose and 0.5 g lukewarm silicon-based antifoaming agent is prepared.

3 g of the clyster preparation (equivalent to 0.3 g paracetamol) are bottled in a graduated clyster flask and supplemented with 5 ml lukewarm water. The reconstitution was attained after 3 minutes. The dissolved active ingredient is available for rapid resorption.

EXAMPLE 7

Dry clyster preparations according to example 2 are bottled in clyster flasks and their long-time stability is tested. After storage over 10 months at room temperature, no significant change in the content of the active ingredient in comparison with the initial value with regard to content and decomposition could be determined.

EXAMPLE 8 (Comparison)

A suspension including:

| | |
|---|---|
| 0.006 g | beclomethasone dipropionate |
| 24.000 g | propylene glycol |
| 2.160 g | p-hydroxybenzoic acid methyl ester |
| 12.000 g | hydroxypropylmethyl cellulose |
| 2.55 g | potassium hydrogen phosphate | ad. 1.20 kg sterile water was adjusted with 2M sodium hydroxide solution.

An almost clear solution was obtained which was bottled by 100 g in PE clyster flasks with screwed plug. A post-examination after 24 months showed that the original content of active ingredient per flask was reduced from 0.5 mg to 0.28 mg.

In contrast thereto, the preparation according to the invention in accordance with example 7 remained stable after 20 months at same storage conditions.

EXAMPLE 9

A man of age 59 with Crohn's disease of the colon ascendens and descendens and strong symptoms was treated unsuccessfully with mesalazine-based finished clysters and hydrocortisone acetate foam. The treatment was continued with beclomethasone clysters according to example 2. After few weeks, the bowel movement per day was reduced by more than half, with the remission being maintained up to the time of the report for already 22 weeks.

Examples 8 and 9 show that clysters of the type according to the invention are not only extraordinarily stable in comparison with conventional finished clysters but also surprisingly effective.

I claim:

1. A method of rectally administering a pharmaceutical preparation to a patient, comprising the steps of:
   preparing a solid composition containing 0.01–95% by weight of an active substance or a mixture of active substances, 99.99 to 5% by weight of adjuvants which includes 2.5 to 50% by weight of a hydrophilic gelatinizing agent and 0.1 to 10% by weight of a waterfree antifoam agent, and a moisture content of less than 15% by weight; and
   reconstituting the solid composition into an aqueous solution, emulsion or suspension before rectal administration to the patient by adding water at room temperature or body temperature.

2. A method as defined in claim 1 wherein said preparing step includes making the composition in form of a solidified melt, or a granulated solid.

3. A method as defined in claim 1 wherein said preparing step includes making the composition in form of a powder having a particle size of less than 1 mm.

4. A method as defined in claim 1 wherein said preparing step includes further adding to the solid composition 0 to 30% by weight of at least one additional adjuvants selected from the group consisting of wetting agent, flow improving agents or buffering agents for standardizing to isotonic or physiological osmotic conditions, as well as 0 to 90% by weight of at least one member selected from the group consisting of a solid PEG having a molecular weight of up to 35,000 and of water-soluble homopolymers or copolymers consisting of or containing repeating units derived from monomers selected from vinylpyrrolidone, vinylacetate or vinylalcohol.

5. A method as defined in claim 1 wherein said preparing step includes adding to the solid composition solid thinning agents and/or nonvolatile liquid constituents.

6. A method as defined in claim 1 wherein said preparing includes providing the solid composition with a moisture content of less than 2% by weight.

7. A method as defined in claim 1, and further comprising storing the solid composition in a graduated clyster flask after said preparing step.

8. A method as defined in claim 1 wherein said reconstituting step includes adding 5 ml or more water to said solid composition.

9. A method as defined in claim 1 wherein said preparing step includes providing an active ingredient selected from the group consisting of beclomethasone, betamethasone, oxipurinol, sulphasalizine and salts, esters, hydrates and other derivatives thereof, and 5-aminosalicylic acid and a salt, an ester and a hydrate thereof.

* * * * *